United States Patent [19]

Carmichael et al.

[11] 4,303,645

[45] Dec. 1, 1981

[54] MODIFIED LIVING CANINE PARVOVIRUS VACCINE

[75] Inventors: Leland E. Carmichael; Max J. G. Appel; Douglas D. McGregor, all of Ithaca, N.Y.

[73] Assignee: Cornell Research Foundation, Inc., Ithaca, N.Y.

[21] Appl. No.: 141,447

[22] Filed: Apr. 18, 1980

[51] Int. Cl.$^3$ .......................................... A61K 39/23
[52] U.S. Cl. ................................... 424/89; 435/235; 435/237
[58] Field of Search .................. 424/89; 435/235–239

[56] References Cited

U.S. PATENT DOCUMENTS

| | | | |
|---|---|---|---|
| 2,136,131 | 11/1938 | Green | 167/78 |
| 2,271,818 | 2/1942 | Green | 167/78 |
| 2,271,819 | 2/1942 | Green | 167/78 |
| 3,133,861 | 5/1964 | Schwarz | 424/89 |
| 3,285,817 | 11/1966 | Slater | 167/78 |
| 3,293,130 | 12/1966 | Slater et al. | 424/89 |
| 3,293,130 | 12/1966 | Slater et al. | 167/78 |
| 3,346,456 | 10/1967 | Baker | 167/80 |
| 3,465,077 | 9/1969 | Baker | 424/89 |
| 3,520,972 | 7/1970 | Smith et al. | 424/89 |
| 3,562,387 | 2/1971 | Lauerman, Jr. | 424/89 |
| 3,577,525 | 5/1971 | Baker | 424/89 |
| 3,709,782 | 1/1973 | Smith et al. | 424/89 |
| 3,733,401 | 5/1973 | Suida | 424/89 |
| 3,869,547 | 3/1975 | Mebus et al. | 424/89 |
| 3,892,627 | 7/1975 | Simons et al. | 424/89 |
| 3,944,469 | 3/1976 | Bittle et al. | 424/89 |
| 4,004,974 | 1/1977 | Chumakov et al. | 424/89 |
| 4,193,990 | 3/1980 | Appel et al. | 424/89 |
| 4,193,991 | 3/1980 | Appel et al. | 424/89 |
| 4,211,843 | 7/1980 | Dubreuil et al. | 424/89 |
| 4,213,965 | 7/1980 | Carmichael | 424/89 |

FOREIGN PATENT DOCUMENTS

| | | |
|---|---|---|
| 1174016 | 7/1964 | Fed. Rep. of Germany. |
| 1426195 | 4/1966 | France. |
| 1286250 | 8/1972 | United Kingdom. |

OTHER PUBLICATIONS

Gagnon et al., Vet. Record, 104:263–264 (1979).
Hayes et al., Can. Vet. J., 29:126 (1979).
Maasab, H. F. et al., P.S.E.B.M. 139:768–773 (1972), Bull. W.H.O. 41:589–594 (1969).
Hayes et al., J.A.V.M.A., 174:1197–1203 (1979).
Johnson et al., Australian Vet. J., 55:151 (1979).
Smorodincev, A. S. Bull. W.H.O. 41:585–588 (1969).
Eugster et al., J.A.V.M.A., 173:1340–1341 (1978).
Burtonboy et al., Arch. Virol., 61:1–12 (1979).
Murphy B. R. et al., J. Inf. Dis. 126(2):170–178 (1972) 28(4):479–487 (1973) 130(2):144–148 (1974).
Bachmann et al., Intervirology, 10:1–16 (1978).
Storz et al., Am. J. Vet Res., 33:269–272 (1972).
Rohita Yodhin, S. et al., J. Immunol. 89:589–597 (1962).
Chapek et al., Modern Vet Pract., Mar. 1981:261–263.
Chappuis et al., Le Point Vet., 10:77–78 (1980).
Dubes, G. H. et al., Virology 4:275–296 (1957).
"A Research Update: Canine Parvovirus" Raltson Purina Company (1980).
Wenner, H. A. et al., J. Hyg. 70:335–350 (1959).
Carp, R. T. et al., P.S.E.B.M. 112:251–256 (1963).
Dubbs, G. R. et al., Virology 4:275–296 (1957).
Markushin, S. G. et al., ACTA Virol. (Prague) 11:100–107 (1967).
Asso, J. et al., Annals Inst. Pasteur Paris 110:233–243 (1966).
Zhidkow, S. A. et al., Veterinariya (Moscow) 10:29–31 (1969).
Bittle, J. L., Chap. 3 "The Devolopment of New Prototype Vaccine Strains" Developments in Industrial Microbiology, vol. 11, Symposium, Cyril J. Corum, Editor, Am. Inst. Biol. Sci., Wash. D.C. (1970).
Appel "Canine Parvovirus Infection" Cornell Research Laboratory for Diseases of Dogs, Laboratory Report, Series 3, No. 1 3/79.
Appel et al., Vet. Record, 105:156–159 (1979).
Appel "Canine Parvovirus" 1978 Proceedings of the Conference of Research Workers on Animal Disease, Nov. 1978.
Appel et al., J.A.V.M.A., 1973:1516–1518 (1978).
Scott et al., Cornell Vet., 60:183–191 (1970).
Pollock et al., Mod. Vet. Practice, 60:375–379 (1979).
Appel et al., Cornell Vet., 69:123–133 (1979).
Cooper et al., Cornell Vet., 69:134–144 (1979).
Black et al., Veternary Medicine/Small Animal Clinician, Jan. 1979:47–50.
Johnson et al., Archiv fur die gesamte Virusforschung, 46:315–324 (1974).
Johnson, J. Small Anim. Practice, 8:319–324 (1967).
Burger et al., Small Animal Clinician, Nov. 1963:611–614.
Burger "The Relationship of Mink Virus Enteritis to Feline Panleucopenia Virus" abstract of Masters Thesis dated prior to 3/66.
Gorham et al., Cornell Vet., 55:554–566 (1965).
Thomson et al., Can. Vet J., 19:346.
Siegel, "The Parvoviruses" in Gard et al., Virology Monographs, 15:1:109 Springer-Verlag.
Binn et al., Infection and Immunity, 1:503–508 (1970).
Eugster et al., The Southwestern Vet., 30:59–60 (1977).

Primary Examiner—Shep K. Rose
Attorney, Agent, or Firm—Jones, Tullar & Cooper

[57] ABSTRACT

A safe, efficacious vaccine for protecting dogs against infection caused by canine parvovirus is produced by prolonged serial passages in non-oncogenic cell lines. One embodiment includes the use of sub-optimal temperatures (below that normal for the dog) during passaging.

18 Claims, No Drawings

MODIFIED LIVING CANINE PARVOVIRUS VACCINE

BACKGROUND OF THE INVENTION

The field of the invention is that of virus vaccines for protection of dogs against infection by canine parvovirus, their production and use.

Parvoviruses are characterized as small animal DNA viruses containing of an isometric protein capsid and a short molecule of single-stranded DNA. Although parvoviruses have been recovered and isolated from various animals, there had been no definite isolation of pathogenic canine parvovirus until recently (Siegl, The Parvoviruses, Springer-Verlag, New York 1976). Bachmann et al. include the dog as a possible parvovirus host in a report detailing the characteristics of parvoviruses in general (Bachmann et al., Intervirology 10: in press, 1978). In 1970, Binn et al. reported the recovery and characterization of a "minute virus of canines" (Binn et al., Infect. Immun. 1: 503, 1970). The isolates described were of canine origin, however, their pathogenicity was not known, and cytopathic effect (CPE) was produced in only a very narrow host range, i.e. only in a single continuous canine cell line, and not in primary canine nor primary or continuous cell cultures from other species. Pathogenicity for dogs was not determined nor was evaluation of vaccine potential done. Based on known properties of the Cornell isolates, it is clear that the recent CPV isolates are not the same as the "minute virus of canines" as described by Binn. In 1977, Eugster and Nairn reported a circumstantially-suggested causative link between diarrhea in puppies and a canine parvovirus. (Eugster, Nairn, Southwestern Veterinarian, 30: 59, 1977). The isolate reported therein could not be serially propagated in MDCK cells, the only cell line tested. Again, pathogenic potential was unexamined and no experimental animal inoculations were performed. In 1978, widespread outbreaks of an apparently new disease in canines appeared (Appel, Cooper, Greisen and Carmichael, JAVMA 173(11) 1516-1518; Dec. 1978), occurring in both the United States and Australia (unpublished). The natural disease is characterized by diarrhea, fever, and leukopenia (relative lymphopenia).

The first isolation of a distinct parvovirus, and its in vitro propagation in primary cells and in cell lines of various species such as mink lung cells and canine kidney was described by two of the inventors in 105 Veterinary Record 156, and in their U.S. Pat. No. 4,193,991, relating to a killed canine parvovirus vaccine.

The factors involved in selective genetic pressure on a virus were described in an article in 20 Infection and Immunity 108, April 1978, Carmichael & Medic, although that article dealt with a different virus (canine herpesvirus). A method of determining virulence through the use of plaque-size was disclosed in Inventor Carmichael's patent application Ser. No. 5,743 filed Jan. 23, 1979, "Small Plaque Variant Canine Herpesvirus Vaccine."

However, although heterotypic (Carmichael, et al, U.S. Pat. No. 4,193,990) and killed vaccines (Carmichael, et al, U.S. Pat. No. 4,193,991) have been known previously, until this invention there has been no successful production of a modified live vaccine for CPV. The production of a modified live CPV vaccine represents a novel and distinct advance in the art. A live virus vaccine constitutes a significant advance over heterotypic and killed vaccines because the magnitude of the immune response represents a 4- or 5-fold improvement over that produced by the other vaccines. The duration of immunity is vastly prolonged, and the live vaccine is commercially easier and cheaper to produce.

SUMMARY OF THE INVENTION AND DESCRIPTION OF PREFERRED EMBODIMENT

The present invention relates to a method of protecting dogs against canine parvovirus. More specifically, the present invention relates to a method of producing a non-virulent attenuated living CPV variant from a native virulent strain of CPV for use as a safe, efficacious vaccine to protect dogs against infection caused by canine parvovirus. The attenuation of the virus is accomplished by prolonged serial passage in non-oncogenic (non-tumor-forming) cell cultures. Dogs vaccinated with the attenuated strain did not suffer illness when challenged by the native strain of CPV.

In the preferred embodiment of the invention, an attenuated live CPV vaccine is produced by serially passaging the native virulent virus (Cornell strain CPV-916) at least 108 times in mink lung and/or dog kidney cell lines at a sub-optimal (lower than that which is normal for the dog) temperature of 33° C.

Other embodiments of the invention include use of other non-oncogenic cell cultures in addition to, or in place of, mink lung or dog kidney cells. An attenuated vaccine is produced with as few as 80 passages, in still another embodiment.

DESCRIPTION OF PROCEDURE AND EXAMPLES

SOURCE OF INITIAL ISOLATE

The virulent native virus isolate used to begin the serial passaging was Cornell type strain 780916 (referred to as CPV-916). This strain (CPV-916) has been placed on deposit at The American Type Culture Collection (ATCC), Rockville, Maryland. The CPV-916 strain may be obtained from ATCC or The James A. Baker Institute for Animal Health, New York State College of Veterinary Medicine at Cornell University, Ithaca, New York. The strain was recovered from the feces and intestinal contents of a Beagle pup that suffered acute diarrheal illness at the Argonne National Laboratories (Sept. 9, 1978). Aggregates of the canine parvovirus (CPV) were initially detected by electron microscopy. Various non-oncogenic cell cultures were inoculated with this material.

CPV-916 was found to grow in a variety of cell types, as did additional CPV strains with indistinguishable properties. Cell cultures that supported growth of CPV were: (1) canine renal cells (primary, secondary, teriary), (2) feline renal cells (primary, Crandell FK cell line), (3) feline lung cell line (CCL 150), (4) Mink lung cell line (CCL 64), (5) MDCK cell line (CCL 34), (6) bovine fetal spleen cells, (7) bovine testicular cells.

The isolate selected for further passage was recovered in secondary dog renal cells prepared from the kidneys of a specific-pathogen-free (SPF) Beagle pup. This primary culture became "Cell Culture Passage #1."

SERIAL PROPAGATION ("PASSAGE") OF CPV-916 AND VIRULENCE TESTS

1. SUMMARY OF TECHNIQUE

Primary or secondary canine renal cells from SPF dogs were chosen initially for serial passage of CPV-916. Initial passages at 3 to 4-day intervals (total of four) were made at 36°-37° C. as undiluted virus. Each passage was monitored for presence of virus by increase in viral hemagglutinin activity (HA titer) and/or positive immunofluoresence (specific for CPV within cell nuclei). After 4 passages, dog inoculations indicated that the virus was virulent. Clinical signs included fever of variable duration (2 to 4 days), lymphopenia, decreased appetite, weight loss, depression, and loose, mucoid feces that sometimes contained blood. Virus at the 4th cell culture passage (referred to as CPV/4) was stored at −70° C. This "virulent virus" was later used for comparative pathogenicity studies and "challenge" of immunized dogs. Infectivity titrations of CPV/4 varied from $10^{6.5}$ to $10^{7.0}$ TCID$_{50}$ per 0.2 ml.

Subsequent passages of CPV (passage 5 and higher) were made at 3 to 5-day intervals using diluted (1:15–1:50) virus. Incubation temperature initially (passages 1–31) was 36° C.; subsequent passages were made at 33° C. At various passage levels, the CPV was inoculated into one or more (usually two or three) Beagle dogs whose susceptibility had been previously determined by absence of hemagglutination-inhibiting (HI) antibody specific for CPV. In each trial, an equal number of littermate dogs was inoculated ("challenged") via oral, intramuscular, or intravenous routes with cell-culture-passaged CPV or CPV/4 (virulent), using similar viral doses and inoculation routes. Clinical and clinical-pathological signs were monitored closely each day and fecal viral shedding profiles were determined. Virus would be considered attenuated (modified in virulence by evidence of reduced pathogenicity) when the following conditions were satisfied: (1) absence of clinical signs in dogs inoculated with passaged virus and presence of signs in littermate control dogs inoculated with the reference (virulent) virus; (2) reduction or absence of viral shedding in the feces of dogs given cell-culture passaged virus as compared with viral shedding profiles of dogs inoculated with reference virus.

2. CPV VIRULENCE AT DIFFERENT PASSAGE LEVELS (See Table 1 for Summary)

PASSAGES-1 THROUGH-30

The CPV was passaged at low (1:15–1:50) dilutions at 3 to 5-day intervals. No significant cytopathic effects were observed in primary or secondary canine renal cells at the time of passage, but viral growth was confirmed at each passage by the presence of intranuclear immunofluorescence, or assay in sensitive cell cultures.

Passage-30 (CPV/30) was tested for virulence by the intravenous inoculation of two 5-month-old SPF Beagles with $10^{6.0}$ TCD$_{50}$ of virus.

Both inoculated dogs had temperature increases (1.5° to 2° C.) on post-inoculation days (PID) 2 and 3. They had slight lymphopenia (PID 4–5), decreased appetites, and slight depression; one dog had a loose, mucoid stool on PID 5. Both had hemagglutination-inhibition (HI) antibody levels of $\geq 5120$ by PID 14. It was thus determined that CPV/30 was still pathogenic for dogs.

PASSAGES-31 THROUGH-51

Additional passages in primary or secondary dog kidney cells continued, but at a reduced temperature (33° C.). This sub-optimal temperature was selected as it was the lowest at which satisfactory CPV growth occurred. Passage of other canine viruses at sub-optimal temperatures has resulted in the selection of variant strains of reduced pathogenicity (Carmichael and Medic, Infection and Immunity 20, 108, Apr. 1978 and U.S. patent application Ser. No. 5,743 filed Jan. 23, 1979, Carmichael Small Plaque Variant Canine Herpesvirus Vaccine). Passage-51 (CPV/51) was examined for virulence and immunogenicity for dogs.

In this trial, two dogs were used. One was inoculated by the subcutaneous+oral/nasal routes with 2 ml of CPV/51. The viral infectivity titer was $10^{6.2}$ per 0.2 ml; the HA titer was 1:512. A sentinel (contact control) dog also was placed with the inoculated dog the following day to monitor viral shedding. Signs were monitored daily for 8 days.

The inoculated dog had slightly elevated temperatures PID 4–6, slight lymphopenia (PID 5 and 6) and a slightly mucoid, loose stool on PID 5. The contact control had a mile febrile resonse on PID 4 and a secondary febrile response on days 7 and 8. Lymphopenia was not detected in the contact animal. Viral shedding was evident from the serological response of the contact dog. By PID 18, both had antibody titers in excess of 1:1280.

Since SPF Beagle dogs have not responded to CPV with severe illness, any sign (slight temperature increase, lymphopenia, inappetence, depression, mucoid stool) was considered as unacceptable virulence for a potential vaccine strain. The slight temperature rise in the contact dog might be considered a pathological response to CPV, since subsequent seroconversion in this animal indicated viral spread from the inoculated dog. No other signs were observed in the contact animal.

PASSAGES 52 THROUGH 79

Continued viral passage was done at 33° C. in canine renal cells. Passages 64 and 73 were titrated and passaged at the endpoint dilutions ($10^{6.2}$ and $10^{6.5}$ TCD$_{50}$ per 0.2 ml, respectively). Other passages were done at 3 to 4-day intervals using diluted (1:50) virus. Cytopathic effects were not evident at the time of each harvest, but viral growth was determined by HA titrations at each passage (as noted above) and periodic infectivity assays by titration in cell cultures.

PASSAGE 80

An additional selective pressure on the virus population was introduced at this time. The 79th passage in dog renal cells (natural host cells) was inoculated into cell cultures derived from an alien host, i.e., mink lung cell line (American Type Culture Collection code CCL-64). This cell line (CCL-64) has been certified as free from mycoplasma, bacteria and fungi. It contains no known latent viruses. We have found it highly susceptible to CPV (Appel, Scott and Carmichael, Veterinary Record 105, 156-159, 1979 and U.S. Pat. No. 4,193,991 Carmichael & Appel, Canine Parvovirus Vaccine). All subsequent passages were performed in CCL-64 cells at 33° C. CPV/80 was propagated at 33°-34° in CCL-64 cells in plastic flasks (75 cm) and harvested after 5 days of growth. The infectivity titer was $10^{5.5}$ TCD$_{50}$/0.2 ml. Tests for virulence in dogs were then performed (Examples 1 and 2).

EXAMPLE 1

Two SPF Beagle dogs (855 and 854) were used. One animal (855) was inoculated intramuscularly with 1 ml of CPV/80; the second dog (854) was placed in contact the following day to monitor viral shedding. One dog (D855) was subsequently challenge-inoculated with CPV/4 to examine protective immunity.

The resulting data is summarized in Table II. The clinical response of D855 to CPV/80 was extremely mild; the possibility of a slight lymphopenia on PID 5 suggested reduced virulence. There was no evidence of enteric disease, but CPV/80 virus was shed to the contact animal (D854). The contact dog developed HI antibody by PID 12, but remained clinically normal. Immunity challenge of D855 with virulent CPV/4, given intravenously 61 days after initial inoculation, indicated complete protection, and there was no shedding of the challenge virus from D855.

A clear reduction in natural virulence was apparent at passage 80, but the slight illness in SPF dogs indicated that this passage was less satisfactory than later (higher) passaged virus.

An additional experiment (Example 2) was therefore designed to further explore reduction in virulence.

EXAMPLE 2

Four littermate SPF Beagles were placed in barrier cages within isolation units and allocated to two groups. One group (dogs 862 and 863) was inoculated with $10^{6.5}$ $TCD_{50}/0.2$ ml (1 ml, intravenously) of CPV/80; dogs in the second group (dogs 863 and 864) each were inoculated by the same route with an identical dose of virulent CPV/4. Clinical responses were noted daily and fecal samples were collected for viral assay.

The resulting data is summarized in Table III. Salient findings were: (1) the clinical responses of the SPF dogs to both virulent and high-passaged (CPV/80) virus were mild, or indistinct. One dog given CPV/80 had a soft stool on PID 4, whilst normal stools were observed in all other animals at all post-inoculation times. Both dogs (864 and 865) given virulent virus had loss of appetite and were depressed on PID 3–4, but they were normal the following day. The dogs given CPV/80 were normal thoughout the observation period.

Of greatest significance were the relative titers of virus found in the feces. Dogs given CPV/80 shed virus from PID 2–7, but the amount of virus shed was less than 1% of that excreted by the dogs given virulent virus (shedding period: PID 2–6). When challenge-inoculated 6 months later, both dogs given CPV/80 were found immune.

Thus, the data suggested clear reduction in original virulence. The findings that CPV/80 was excreted later than CPV/4 and that amounts of excreted high-passaged virus were drastically reduced ($<1\%$) were especially significant. Reduced viral growth in a standard host may be taken as an indication of attenuation.

PASSAGES 81 THROUGH 108

Continued passage was done in CCL-64 cells at 3 to 4-day intervals. Passage 108 had an infectivity titer of $10^{7.5}$ $TCD_{50}/0.2$ ml. At that passage tests for virulence were done in outbred (not SPF) Beagle dogs obtained from a seronegative (susceptible) research kennel located in Ithaca, N.Y. Preliminary studies indicated that (unlike SPF dogs) animals from this kennel suffered more pronounced illness after inoculation with CPV/4 by the oral or intravenous routes. These dogs were used in Examples 3 and 4.

EXAMPLE 3

Six littermate dogs were divided into two isolated groups of 3 dogs each and then inoculated with CPV/108 or CPV/4. Two dogs in each group were given virus intramuscularly; one dog in each group was oral-nasally inoculated. The viral doses (1 ml) were: CPV/108$=10^{8.2}$ $TCD_{50}$; CPV/4$=10^{7.7}$ $TCD_{50}$. Dogs were studied daily for clinical signs, viral shedding in the feces, and serological responses.

The resulting data is summarized in Table IV. The clinical-pathological responses of the dogs clearly discriminated between CPV/108 and virulent CPV/4. Animals given CPV/108 did not have clinical signs; all gained weight and they developed high levels of HI antibody by PID 7. Viral shed in feces occurred with CPV/108, but amounts were less than 0.5% of the quantity shed (time of maximal excretion) by the dogs given CPV/4. The period of viral shedding also was less. In contrast to the vaccinated dogs, all dogs given virulent CPV/4 became severely ill; one dog (R-6) died on PID 10. Despite severe illness (inappetence, weight loss, severe depression on PIDs 6–9, and pasty, mucoid feces with blood), dogs R-4 and R-5 made rapid recoveries and were normal on PID 11. They remained gaunt for $>1$ week. None had fever. Surprisingly, there was pronounced hypothermia in the most severely affected dogs.

This experiment indicated that attenuation of original virulence had occurred by passage 108. Characteristics of a suitable vaccine candidate strain seem satisfied at this passage level.

EXAMPLE 4

Immunogenicity of CPV/108 from dogs given $10^{5.2}$ $TCD_{50}$ by the intramuscular route was evaluated by challenge of immunity 28 days later. Serological and protective immune responses were evaluated. A sentinal animal (D890) was included to monitor viral shed in the feces. Results are recorded in Table V.

All three inoculated dogs remained healthy and developed high levels of HI antibody by PID7. They were immune following challenge with virulent CPV/4. The contact animal remained normal but had HI antibody at PID 14. Virus shed from vaccinates to the contact dog, rendering it immune, though not directly injected.

EXAMPLE 5

Passage 115 (CPV/115)

Additional examination of virulence of high-passaged CPV was done at passage level 115 (CCL-64 cells; 33° C.). Four outbred (non-SPF) 8-week-old Beagle pups were placed in separate isolation cages. Two pups (D870 and 871) were inoculated intravenously with 5 ml of CPV/115 ($10^{7.0}$ $TCD_{50}/0.2$ ml); two pups were given 5 ml of CPV/4 ($10^{6.5}$ $TCD_{50}/0.2$ ml) by the same route.

The two dogs given CPV/115 remained clinically normal throughout a 2-week observation period. In contrast, the pups given virulent virus both had mucoid, bloody feces and had febrile responses on PID 3–4. They were markedly depressed, unresponsive, and had inappetence on PID 3–6. There was only slight lymphopenia, but their erythrocyte sedimentation rates were increased, a clear sign of disease. Whereas dogs 870 and 871 (CPV/115-inoculated) gained approximately 1 lb during the first week after infection, dogs 872 and 873 (CPV/4-inoculated) lost 10% of their initial body weights. Recovery was rapid, commencing on PID 6, but normal weights were not regained until 2 weeks later.

Pronounced differences in fecal shedding patterns also were found. Table VI illustrates comparative viral shedding patterns in the feces of dogs given CPV/4 or CPV/115. All dogs developed high HI antibody by PID 7.

When challenge-inoculated by the oral route as a test of immunity 3 weeks after vaccination, all dogs innoculated with CPV/115 were found immune. There was no illness, and virus was not shed in the feces.

Thus, it is shown that canine parvovirus at passage 115 (CPV/115) did not cause any signs of illness, but it engendered a protective immune response to virulent (CPV/4) virus.

While in the foregoing description the detailed embodiments of the present invention have been set forth, it will be understood by those skilled in the art that considerable variation may be made in such detail without departing from the spirit of our invention.

TABLE I

Response of Beagle Dogs to Canine Parvovirus (Cornell Strain 916) at Various Cell Culture Passage Levels.

| Cell culture passage level | Inappetence (p.i.days) | Elevated temp. (p.i.days) | Lymphopenia (p.i.days) | Mucoid or bloody stool (p.i.days) | Weight loss | Death (p.i.day) | Viral shed in feces | Pathogenicity** | Remarks |
|---|---|---|---|---|---|---|---|---|---|
| Passage-4* (35–36° C.) | 7/7 (3–6) | 5/7 (3–4) | 3/5 (3–5) | 5/7 (4–10) | 3/7 | 1/7 | Yes (3–10) | +++ | Virulent |
| Passage-30 (35–36° C.) | 2/2 (3–5) | 2/2 (4–6) | 2/2 (4–5) | 1/2 (5–6) | Not done | 0/2 | Yes (3–7) | +++ | Virulent |
| Passage-51 (33° C.) | 0/1 | 1/1 (4) | 1/1 (4–5) | 0/1 | 0/1 | 0/1 | Yes (4–7) | + or ± | Unacceptable virulence |
| Passage-80 (33° C.) | 0/2 | 0/2 | Not done | 0/2 | 0/2 | 0/2 | Yes (3–7) | − | Reduced virulence |
| Passage-108 (33° C.) | 0/3 | 0/3 | Not done | 0/3 | 0/3 | 0/3*** | Yes (3–7) | − | Avirulent |
| Passage-115 (33° C.) | 0/2 | 0/2 | 0/2 | 0/2 | 0/2 | 0/2**** | | − | Avirulent |

*Various passage levels inoculated by intravenous route into S.P.F. Beagle pups less than 13 weeks of age. Viral dose varied from $10^{6.5}$ $TCD_{50}$/ml to $10^{7.5}$ $TCID_{50}$. In each experiment, at least 1 littermate control dog received virulent (CPV/4) virus.

**Pathogenicity score + − +++ refers to degree of illness or signs following infection.

***All (3) control littermates given CPV/4 became very sick, 1 died on dpi 10. Clear difference between CPV/3 and CPV/108 demonstrated.

****Control littermates (2 dogs) developed bloody, mucoid diarrhea p.i. days 3–4; had severe depression and weight loss. Clear demonstration of reduced pathogenicity of CPV/115 versus CPV/4.

TABLE II

Test of Virulence (CPV/80) in Dogs

| | D855C (inoculated)* | | | | D854 (contact) | | | |
|---|---|---|---|---|---|---|---|---|
| Day post-inoc. (IM) | Temp. °C. | Leukocytes (% lympho.) | Feces | H-I antibody | Temp. °C. | Leukocytes (% lympho.) | Feces | H-I antibody |
| −1 | 101.5 | 11.7(8.4) | Normal | <10 | — | — | — | — |
| +1 | 101.2 | 11.2(8.2) | " | — | — | — | — | — |
| 2 | 101.8 | 16.9(6.7) | " | — | 101.5 | — | Normal | <10 |
| 3 | 101.5 | — | " | — | 101.0 | — | " | |
| 4 | 101.5 | 10.9(5.5)** | " | 40 | 101.7 | — | " | |
| 5 | 102.2 | 14.2(4.5) | " | 160 | 100.8 | — | " | |
| 6 | 100.8 | 12.0(6.0) | " | 1280 | 101.5 | — | " | |
| 7 | 101.2 | 14.2(7.1) | " | 2560 | 101.8 | — | " | <10 |
| ↓ | | | | | | | | |
| | 101.7 | — | " | 2560 | 101.8 | — | " | 640 |
| | Immunity Challenge (IV) with virulent CPV*** | | | | | | | |
| ↓ | | | | | | | | |
| 61 | 101.0 | — | Normal | 5120 | | Terminate | | |
| 62 | 101.2 | — | " | — | | | | |
| 63 | 101.2 | — | " | — | | | | |
| 64 | 101.8 | 14.0(6.7) | " | — | | | | |
| 65 | 101.0 | — | " | — | | | | |
| 66 | 101.2 | 17.1(7.2) | " | — | | | | |
| 67 | 101.8 | — | " | 2560 | | | | |

*Dog 855 inoculated intramuscularly (IM) with 1 ml (>$10^{5.5}$ $TCD_{50}$) of CPV/80. The following day D854 placed as in-unit contact to assess viral shedding from D855.

**Possible lymphopenia for this dog, but within normal range. Very slight temperature response on dpi 5.

***Immunity challenge 3 weeks post-vaccination with CPV/80. Dog given ≧ $10^7$ $TCD_{50}$ virulent CPV by intravenous (IV) route. No illness observed at any time.

TABLE III

Disease and Fecal Shedding Patterns of CPV/80 Versus Virulent CPV/4

| | CPV/80 (I-V inoculation)* | | | | | | | | CPV/4 (I-V inoculation) | | | | | | | |
|---|---|---|---|---|---|---|---|---|---|---|---|---|---|---|---|---|
| | Dog 862 | | | | Dog 863 | | | | Dog 864** | | | | Dog 865 | | | |
| Post-inoc. day | Temp. °F. | Feces | Fecal CPV titer*** | HI anti-body | Temp. °F. | Feces | Fecal CPV titer | HI anti-body | Temp. °F. | Feces | Fecal CPV titer | HI anti-body | Temp. °F. | Feces | Fecal CPV titer | HI anti-body |
| 1 | 101.6 | Normal | <1.0 | <10 | 101.2 | Normal | <1.0 | <10 | 101.5 | Normal | <10 | <10 | 101.6 | Normal | <10 | <10 |
| 2 | 101.0 | " | <1.0 | — | 101.9 | " | <1.0 | — | 101.4 | " | 4.0 | — | 102.0 | " | 4.0 | — |
| 3 | 101.0 | " | 3.0 | <10 | 101.5 | " | 3.0 | <10 | 101.5 | " | ≧9.0 | <10 | 102.2 | " | — | <10 |
| 4 | 101.6 | Slightly soft | 5.2 | 160 | 101.6 | " | 4.5 | 40 | 101.0 | " | 7.0 | 80 | 102.3 | " | ≧9.0 | 80 |
| 5 | 101.3 | Normal | 6.5 | 320 | 101.0 | " | 5.8 | 640 | 102.2 | " | 6.5 | 1280 | 103.0 | " | 6.0 | 1280 |
| 6 | 101.6 | " | 5.2 | 1280 | 101.7 | " | 4.5 | ≧10,240 | 101.2 | " | <1.0 | >10,240 | 102.3 | " | <1.0 | >10,240 |
| 7 | 101.8 | " | <1.0 | 5120 | 101.4 | " | <1.0 | 10,240 | 101.6 | " | <1.0 | 10,240 | 101.8 | " | <1.0 | 10,240 |
| 8 | 101.8 | " | <1.0 | — | 101.2 | " | <1.0 | — | 101.2 | " | <1.0 | — | 101.0 | " | <1.0 | — |
| 9 | 101.1 | " | <1.0 | — | 101.0 | " | <1.0 | — | 101.2 | " | <1.0 | — | 101.3 | " | <1.0 | — |
| 10 | 101.8 | " | <1.0 | — | 100.0 | " | <1.0 | — | 100.8 | " | <1.0 | — | 101.5 | " | <1.0 | — |
| 11 | 102.0 | " | <1.0 | — | 101.0 | " | <1.0 | | 101.0 | " | <1.0 | — | 101.6 | " | <1.0 | — |
| 12 | — | " | — | — | — | " | — | — | — | " | — | — | — | " | — | — |
| 13 | — | " | — | — | — | " | — | — | — | " | — | — | — | " | — | — |
| 14 | — | " | — | 5120 | — | " | — | 5120 | — | " | — | 5120 | — | " | — | 10,240 |
| | Oral Challenge with Virulent Virus | | | | | | | | | | | | | | | |
| 180–187 | 101.5–101.8 | Normal | Neg. | 640 | 101.8–102.0 | Normal | Neg. | 640 | | | | | | | | |
| 188 | — | " | " | | — | " | | | | | | | | | | |

*SPF littermate Beagle pups inoculated intravenously (I-V) with either CPV/80 or virulent CPV (CPV/4). In both instances viral titers were $10^{6.5}$/0.2 ml $TCD_{50}$.
**Neither dog given virulent virus had clinical signs of enteritis, but both had anorexia, depression and were unresponsive p.i. days 3 and 4. None lost significant weight.
***Fecal CVP titer means $\log_{10}$ titer of infectious CPV per gm. feces, assayed in A/72 canine fibroblastic cells. Maximal viral titers are indicated by underline.

TABLE IV

Disease Signs and Fecal Shedding Patterns of CPV/108 Versus Virulent CPV/4

CPV Passage-108

| Post-inoc. day | Dog R-1 (I-M)* | | | | Dog R-2 (I-M) | | | | Dog R-3 (Oral/Nasal) | | | |
|---|---|---|---|---|---|---|---|---|---|---|---|---|
| | Temp. °F. | Clinical illness | Fecal CPV titer (isol.) | HI antibody | Temp. °F. | Clinical illness | Fecal CPV titer (isol.) | HI antibody | Temp. °F. | Clinical illness | Fecal CPV titer (isol.) | HI antibody |
| 1 | 101.6 | —** | <20(—)*** | <10 | 101.0 | — | 10(—) | <10 | 101.4 | — | 20(—) | <10 |
| 2 | 100.6 | — | <10(+) | — | 100.7 | — | 20(+) | — | 100.5 | — | 10(+) | — |
| 3 | 100.4 | — | 40(+) | 10 | 100.6 | — | 40(+) | 10 | 100.7 | — | ≦10(+) | <10 |
| 4 | 101.0 | — | — | — | 101.4 | — | — | — | 100.9 | — | — | — |
| 5 | 100.0 | — | 160(+) | 640 | 100.5 | — | 160(+) | 640 | 100.4 | — | 160(+) | 320 |
| 6 | 99.8 | — | — | — | 100.6 | — | — | — | 100.0 | — | — | — |
| 7 | 100.0 | — | 40(+) | 10,240 | 100.0 | — | 20(—) | 5120 | 100.1 | — | 10(+) | 10,240 |
| 8 | 100.0 | — | — | — | 101.4 | — | — | — | 100.6 | — | — | — |
| 9 | 100.6 | — | — | — | 100.4 | — | — | — | 100.5 | — | — | — |
| 10 | 100.8 | — | ≧20(—) | 10,240 | 99.4 | — | <10(—) | 5120 | 100.3 | — | 10(—) | 10,240 |

Virulent CPV (passage 4)

| Post-inoc. day | Dog R-4 (I-M) | | | | Dog R-5 (I-M) | | | | Dog R-6 (Oral/Nasal) | | | |
|---|---|---|---|---|---|---|---|---|---|---|---|---|
| | Temp. °F. | Clinical illness | Fecal CPV titer (isol.) | HI antibody | Temp. °F. | Clinical illness | Fecal CPV titer (isol.) | HI antibody | Temp. °F. | Clinical illness | Fecal CPV titer (isol.) | HI antibody |
| 1 | 101.0 | — | 10(—) | <10 | 101.0 | — | <10(—) | <10 | 100.4 | — | 20(—) | <10 |
| 2 | 101.0 | — | <10(—) | <10 | 100.8 | — | 40(—) | <10 | 101.4 | — | 10(+) | — |
| 3 | 100.8 | — | 160(+) | <10 | 102.0 | — | 2560(+) | <10 | 101.1 | — | 160(+) | <10 |
| 4 | 101.0 | — | — | — | 101.6 | — | — | — | 101.0 | — | — | — |
| 5 | 101.4 | — | >20,480(+) | 640 | 101.0 | + | >20,480(+) | 640 | 101.4 | + | >20,480(+) | 20 |
| 6 | 100.8 | + | — | — | 99.8 | ++ | — | — | 101.4 | ++ | — | — |
| 7 | 100.4 | ++ | 320(+) | 10,240 | 98.8 | +++ | 320(+) | 10,240 | 100.1 | ++ | >10,240(+) | 20 |
| 8 | 99.0 | + | — | — | 98.6 | ++ | — | — | 99.2 | +++ | — | — |
| 9 | 100.2 | + | — | — | 100.7 | ++ | — | — | 98.9 | +++ | — | — |
| 10 | 100.8 | ± | 80(+) | 5120 | 100.0 | ± | 80(—) | 5120 | <95 | Died | (+) | — |
| 11 | 100.0 | — | — | — | 101.1 | — | — | — | | | | |

*Dogs R-1, R-2, R-4, and R-5 inoculated by intramuscular (I-M) route, dogs R-3 and R-6 given virus by oral/nasal route. Viral titers: CPV/108 = $10^{7.5}/0.2$ ml; CPV/4 = $10^{7.0}/0.2$ ml.
**Clinical illness was not observed(—) in R-1, R-2, or R-3 dogs at any time; signs (+ to +++) in dogs R-4 and R-5 were pasty, mucoid feces with blood (dpi 5-10), depression, inappetence, and weight loss amounting to >10% body weight over a 6-day period. Dog R-6 died on p.i. day 10, with typical microscopic lesions of CPV.
***Fecal titers represent CPV hemagglutinin activity. Viral isolation indicated by (+ = pos.) or (— = neg.).

TABLE V

Immune Response of Dogs to CPV/108 (Intramuscular Inoculation) and Viral Shed

| Dog | Status* | H-I Antibody Titer Post-inoculation day | | | | Response to challenge (PID 28)** |
|---|---|---|---|---|---|---|
| | | Pre | 7 | 14 | 21 | |
| 880 | Vac. | <10 | 5120 | 2560 | 2560 | Immune |
| 881 | Vac. | <10 | 1280 | 2560 | 2560 | Immune |
| 882 | Vac. | <10 | 2560 | 2560 | 1280 | Immune |
| 883 | Contact | <10 | 10 | 1280 | 1280 | Immune |

*Dogs (880, 881, 882) vaccinated (Vac.) with $10^{5.2}$ TCD$_{50}$ of CPV/108 by intramuscular route. Dog 883 placed in contact with vaccinates to monitor viral shed.
**Dogs judged immune if there was no illness, seroconversion, or fecal viral shed following oral-nasal inoculation with $10^{6.5}$ TCD$_{50}$ of CPV/4 (virulent).

TABLE VI

Response of Dogs to Canine Parvovirus Passage 115 (CPV/115) Versus Passage (CPV/4)

Virus Inoculation

| | CPV/115* (Vaccinal Candidate) | | | | | | | | CPV/4 (Virulent) | | | | | | | |
|---|---|---|---|---|---|---|---|---|---|---|---|---|---|---|---|---|
| | Dog 870 | | | | Dog 871 | | | | Dog 872 | | | | Dog 873 | | | |
| | Fecal Virus Titer** | | Serum H-I Anti-body | Clin-ical Signs | Fecal Virus Titer | | Serum H-I Anti-body | Clin-ical Signs | Fecal Virus Titer | | Serum H-I Anti-body | Clin-ical Signs | Fecal Virus Titer | | Serum H-I Anti-body | Clin-ical Signs |
| Post Inoc Day | HA | Infect. | | | HA | Infect. | | | HA | Infect. | | | HA | Infect. | | | |
| 1 | ≦20 | <2 | <10 | — | <20 | <2 | <10 | — | <20 | <2 | <10 | — | <20 | <2 | <10 | — |
| 2 | <20 | <2 | — | — | <20 | <2 | — | — | <20 | <2 | — | — | <20 | <2 | — | — |
| 3 | <20 | ≧2 | — | — | <20 | ≧2 | — | — | 320 | ≧2 | — | + | 20 | ≧2 | — | + |
| 4 | 20 | 5.5 | — | — | 20 | 4.5 | — | — | >327,680 | 8.2 | — | +++ | ≧327,680 | 8.7 | — | +++ |
| 5 | <20 | 5.5 | — | — | 80 | 3.5 | — | — | >327,680 | 9.7 | — | +++ | ≧327,680 | 8.7 | — | +++ |
| 6 | 20 | 4.5 | — | — | 640 | 3.5 | — | — | >327,680 | 9.0 | — | +++ | ≧327,680 | 8.2 | — | + |
| 7 | 320 | 4.5 | 2560 | — | 640 | ≧2 | 1280 | — | 10,240 | >2 | 5120 | + | <20 | ≧2 | 5120 | — |
| 8 | 160 | 2 | — | — | 80 | <2 | — | — | 320 | ≧2 | — | — | <20 | <2 | — | — |
| 9 | <20 | <2 | — | — | <20 | <2 | — | — | <20 | <2 | — | — | <20 | '2 | — | — |
| 10 | <20 | <2 | 5120 | — | <20 | <2 | 5120 | — | <20 | <2 | 5120 | — | <20 | <2 | 5120 | — |
| 14 | — | — | | | — | — | | | — | — | | | — | — | | |
| 21 | — | — | | | — | — | | | — | — | | | — | — | | |
| Post-chall. Day | Challenge Inoculation (CPV/4 by oral-nasel route)+ | | | | | | | | | | | | | | | |

TABLE VI-continued

Response of Dogs to Canine Parvovirus Passage 115 (CPV/115) Versus Passage (CPV/4)

Virus Inoculation

| | CPV/115* (Vaccinal Candidate) | | | | | | CPV/4 (Virulent) | | | | | |
|---|---|---|---|---|---|---|---|---|---|---|---|---|
| | Dog 870 | | | Dog 871 | | | Dog 872 | | | Dog 873 | | |
| | Fecal Virus Titer** | | Serum H-I Antibody | Fecal Virus Titer | | Serum H-I Antibody | Fecal Virus Titer | | Serum H-I Antibody | Fecal Virus Titer | | Serum H-I Antibody |
| | HA | Infect. | Clinical Signs | HA | Infect. | Clinical Signs | HA | Infect. | Clinical Signs | HA | Infect. | Clinical Signs |
| 1 | ≦20 | — | 5120 | <20 | — | 2560 | | | | | | |
| 2 | — | | — | — | | — | | | | | | |
| 3 | ≦20 | <2 | — | <20 | <2 | — | | | | | | |
| 4 | — | | — | — | | — | | | | | | |
| 5 | <20 | <2 | — | <20 | <2 | — | | | | | | |
| 6 | — | | — | — | | — | | | | | | |
| 7 | <20 | — | 2560 | <20 | — | 2560 | | | | | | |

*Dogs inoculated by intravenous route with either $10^{6.5}$ TCD$_{50}$(CPV/4) or $10^{7.5}$ TCD$_{50}$ (CPV/115).
**Fecal virus titer expressed as hemagglutinating (HA) units or infectivity (Infect.)/gm feces.
***Clinical signs negative (—) or present (graded + to +++). Three-plus means fever, depression, anorexia, mucoid and blood-tinged stool.
+Only dogs given CPV/115 challenge-inoculated.

We claim:

1. A method of protecting dogs from infection caused by canine parvovirus comprising inoculating an animal with modified living canine parvovirus vaccine (CPV) prepared in accordance with a procedure which comprises taking a seed of a virulent CPV strain and serially passaging the strain in non-oncogenic cell cultures at a sub-optimal temperature at which CPV growth occurs until a non-virulent, immunizing virus is produced.

2. The method of claim 1 in which the serial passaging comprises at least 80 passages.

3. The method of claim 2 in which the serial passaging comprises 108 passages.

4. The method of claim 1 in which the passage temperature is approximately 33° C.

5. The method of claim 1 in which the nononcogenic cell culture consists of a medium selected from the group consisting of MDCK cell line (CCL-34), canine kidney cells, mink lung cells, bovine fetal spleen cells, bovine testicular cells, feline lung cells, or feline renal cells.

6. The method of claim 1 in which the virulent CPV strain is CPV-916.

7. A modified live vaccine for protecting dogs against infection caused by canine parvovirus produced by a process comprising the steps of taking a seed of a virulent CPV strain and serially passaging the strain in non-oncogenic cell cultures at a sub-optimal temperature at which CPV growth occurs with periodic tests until a non-virulent strain is produced.

8. The vaccine of claim 7 in which the serial passaging comprising at least 80 passages.

9. The vaccine of claim 8 in which the serial passaging comprises 108 passages.

10. The vaccine of claim 7 in which the passage temperature is approximately 33° C.

11. The vaccine of claim 7 in which the non-oncogenic cell culture consists of a medium selected from the group consisting of MDCK cell line (CCL-34), canine kidney cells, mink lung cells, bovine fetal spleen cells, bovine testicular cells, feline lung cells, or feline renal cells.

12. The vaccine of claim 7 in which the virulent CPV strain is CPV-916.

13. The method of producing a modified live vaccine for protecting dogs against canine parvovirus comprising the steps of:
 a. Starting with a seed of virulent CPV;
 b. Serially passaging the virus in non-oncogenic cell cultures at a sub-optimal temperature at which CPV growth occurs;
 c. Periodically testing the passaged virus for virulence until a non-virulent virus is produced.

14. The method of claim 13 in which the serial passaging comprises at least 80 passages.

15. The method of claim 14 in which the serial passaging comprises 108 passages.

16. The method of claim 13 in which the passage temperature is approximately 33° C.

17. The method of claim 13 in which the nononcogenic cell culture consists of a medium selected from the group consisting of MDCK cell line (CCL-34), canine kidney cells, mink lung cells, bovine fetal spleen cells, bovine testicular cells, feline lung cells, or feline renal cells.

18. The method of claim 13 in which the virulent CPV strain is CPV-916.

* * * * *